(12) United States Patent
Kabin et al.

(10) Patent No.: US 7,115,791 B2
(45) Date of Patent: Oct. 3, 2006

(54) METHOD AND APPARATUS FOR CONTROLLING EFFLUENT COMPOSITION IN OXYGENATES TO OLEFINS CONVERSION

(75) Inventors: Jeffrey Alan Kabin, Houston, TX (US); Nicolas P. Coute, Houston, TX (US); Stephen N. Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 558 days.

(21) Appl. No.: 10/325,523

(22) Filed: Dec. 19, 2002

(65) Prior Publication Data

US 2004/0122273 A1   Jun. 24, 2004

(51) Int. Cl.
*C07C 1/00* (2006.01)
*C07C 2/00* (2006.01)

(52) U.S. Cl. .............. 585/640; 585/639; 585/501; 585/956

(58) Field of Classification Search ........ 585/638–640, 585/501, 956
See application file for complete search history.

(56) References Cited

U.S. PATENT DOCUMENTS

| | | | |
|---|---|---|---|
| 4,076,796 A | 2/1978 | Reh et al. | |
| 5,157,181 A | 10/1992 | Stine et al. | |
| 5,407,830 A | 4/1995 | Altman et al. | 436/55 |
| 5,470,482 A | 11/1995 | Holt | 210/662 |
| 5,862,060 A | 1/1999 | Murray, Jr. | 364/528.01 |
| 5,952,538 A | 9/1999 | Vaughn et al. | |
| 6,023,005 A | 2/2000 | Lattner et al. | |
| 6,103,934 A | 8/2000 | Hallinan et al. | 562/517 |
| 6,137,022 A | 10/2000 | Kuechler et al. | |
| 6,162,644 A | 12/2000 | Choi et al. | 436/55 |
| 6,166,282 A * | 12/2000 | Miller | 585/638 |
| 6,228,650 B1 | 5/2001 | Moore et al. | 436/55 |
| 6,287,522 B1 | 9/2001 | Lomas | |
| 6,420,595 B1 | 7/2002 | Hallinan et al. | |

FOREIGN PATENT DOCUMENTS

| EP | 157 181 | 10/1985 |
|----|---------|---------|
| EP | 490 742 | 6/1992 |

OTHER PUBLICATIONS

Qin et al., "Quantitative Analysis of Process Streams by On-Line FT-IR Spectrometry." *Anal. Chem.* vol. 69, pp. 1942-1945 (1997).
Fluidization and "Fluid-Particle Systems," Frederick A. Zenz et al., pp. 48-59, 1960.
"Kinetic Modeling of Methanol Transformation into Olefins on a SAPO-34 Catalyst," Ana G. Gayubo et al., Ind. Eng. Chem. Res., vol. 39, pp. 292-300, 2000.

* cited by examiner

*Primary Examiner*—Glenn Caidarola
*Assistant Examiner*—In Suk Bullock

(57) ABSTRACT

A process for controlling an oxygenates to olefin reactor is disclosed which comprises: contacting oxygenate-containing feedstock, e.g., methanol, in a reaction zone in the presence of a molecular sieve oxygenate to olefins conversion catalyst under conditions sufficient to provide an olefins-containing effluent containing alkyl alcohol and dialkyl ether, e.g., methanol and dimethyl ether; analyzing a single gas phase of the effluent determine alkyl alcohol concentration and dialkyl ether concentration; and adjusting reactor conditions, e.g., WHSV, as a function of alkyl alcohol concentration and dialkyl ether concentration, as necessary to provide a substantially consistent effluent composition. A corresponding apparatus for carrying out the process is also provided.

43 Claims, 2 Drawing Sheets

METHOD AND APPARATUS FOR CONTROLLING EFFLUENT COMPOSITION IN OXYGENATES TO OLEFINS CONVERSION

FIELD

The present invention relates to an oxygenates to olefins reactor apparatus employing a fluid bed reactor and a process for its control.

BACKGROUND

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

Important alternate feeds for the production of light olefins are oxygenates, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The process for converting a feedstock, especially a feedstock containing one or more oxygenates, in the presence of a molecular sieve catalyst composition according to the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In a preferred embodiment of oxygenates to olefins conversion, a fluidized bed process or high velocity fluidized bed process is employed which includes a reactor system, a regeneration system and a recovery system.

In order to optimize operation of oxygenates conversion to light olefins, it is desirable to control various parameters associated with the oxygenate to olefins conversion reactor. Such control can enhance oxygenate conversion and/or selectivity for prime olefins, especially for ethylene and propylene.

U.S. Pat. No. 6,166,282 to Miller teaches a process for converting oxygenates to light olefins in a fast-fluidized bed reactor and further observes that oxygenate conversion processes can be sensitive to reaction variables such as temperature, catalytic activity, and space velocity.

U.S. Pat. No. 5,952,538 to Vaughn et al. discloses an optimal range of space velocities which are suitable for oxygenates to olefin conversion.

Gayubo, et al, *Ind. Eng. Chem. Res.* 2000, 39, 292–300, disclose that in conversion to olefins, higher average reaction temperatures at a given coke level on the catalyst increases selectivity to ethylene.

U.S. Pat. No. 6,137,022 to Kuechler et al. discloses oxygenates to olefins conversion in the presence of silicoaluminophosphate molecular sieve-containing catalyst which maintains an optimal feedstock conversion between 80% and 99% under conditions effective to convert 100% of the feedstock when the reaction zone contains at least 33 volume percent of the silicoaluminophosphate molecular sieve.

U.S. Pat. No. 6,023,005 discloses the importance of maintaining optimal average coke levels on oxygenates to olefins conversion catalyst to effect improved lower olefin selectivity.

Infrared (IR) analysis of various process streams for the purpose of process control is known in the prior art.

U.S. Pat. No. 6,103,934 to Hallinan et al. discloses a process control method for producing acetic acid by catalyzed carbonylation of methanol in which various reactor component concentrations, e.g., active catalyst, methyl iodide, water and methyl acetate are measured using an infrared analyzer. The concentrations are adjusted in response to the measurements taken to optimize the acetic acid reaction.

U.S. Pat. No. 6,228,650 to Moore et al. discloses controlling concentration of alkylation catalyst components HF acid, acid soluble oil (ASO) and water, by measuring a continuously flowing catalyst slip stream in an IR analyzer and using the results to vary temperature of stripping fluid in order to control ASO levels within a preferred range.

U.S. Pat. No. 6,162,644 to Choi et al. teaches controlling separation and isomerization of xylene isomer by analyzing various streams provided by the process using near IR (NIR). The analysis results are utilized for on-line monitoring, process control and process optimization for producing para-xylene.

U.S. Pat. No. 5,862,060 to Murray, Jr. discloses controlling chemical processes using compositional data, as the basis for control using NIR spectroscopy which allows for on-line measurements in real time. A calibration set of NIR spectra bounding the acceptable process space for a particular controlled property is assembled and a multivariant statistical method is applied to the calibration step to identify a small number (2–4) of the characteristics of the set governing the controlled property. Thus a complex process can be controlled in such a way as to provide a substantially invariant product composition.

Deru Qoin et al., "Quantitative Analysis of Process Streams by Online FTIR Spectrometry," Anal. Chem (1997), 69(10), 1942–1945, teaches an online method for real-time characterization of gas streams containing trimethylamine and methanol using Fourier Transform Infrared (FT-IR) spectrometry with multivariate methods, e.g., partial least squares, to obtain quantitative information for process control.

U.S. Pat. No. 5,470,482 to Holt teaches controlling para-xylene purity or recovery in a moving bed para-xylene separation process. The process measures concentrations of para-xylene, meta-xylene, ortho-xylene, and ethylbenzene in various streams by NIR or mid-range FT-IR and operating variables adjusted in response.

U.S. Pat. No. 5,407,830 discloses control of catalyst composition in an HF alkylation unit by sampling and analyzing feedstreams using infrared spectroscopy to generate signals which are compared to reference signals in order to generate difference signals which control the flow of individual reactor feed components.

All of the foregoing references are incorporated by reference herein in their entirety.

Variations over time in oxygenate to olefins reactor effluent composition can cause difficulties in subsequent effluent processing required to obtain products which meet the requirements for desired end uses. Effluent stream fluctuations in composition can overload separations used to obtain polymer grade olefin streams, resulting in products which are outside the desired specification, e.g., containing unacceptably high levels of oxygenate, or highly unsaturated olefins such as diolefins and acetylenes. The present invention provides a simple and effective method for controlling oxygenates to olefins reactor systems so that a consistent reactor effluent stream can be obtained. While the extent of oxygenates conversion can be determined from many types of effluent stream analyses, it is difficult to obtain such an analysis fast enough for the results to be useful for oxygenates to olefins reactor control. Accordingly, it would be desirable to provide a process for controlling an oxygenates to olefin reactor which provides a substantially consistent effluent stream, by sampling the product stream to determine the extent of oxygenate conversion. In particular, it would be desirable to sample and analyze effluent samples within a time frame sufficient to provide effluent analysis results that can be used to control reactor conditions, in order to maintain a substantially consistent effluent.

SUMMARY

In one aspect, the present invention relates to a process for controlling an oxygenates to olefin reactor to provide a substantially consistent effluent composition, which process comprises: contacting an oxygenate-containing feedstock in a reaction zone in the presence of a molecular sieve oxygenate to olefins conversion catalyst under reaction conditions sufficient to provide an olefins-containing effluent containing alkyl alcohol and dialkyl ether; analyzing a single gas phase of the olefins-containing effluent containing alkyl alcohol and dialkyl ether to determine alkyl alcohol concentration and dialkyl ether concentration of said effluent; adjusting the reactor conditions as a function of the alkyl alcohol concentration and the dialkyl ether concentration, as necessary to provide the substantially consistent effluent composition.

In one embodiment of this aspect of the invention, the oxygenate-containing feedstock comprises methanol, the alkyl alcohol is methanol and the dialkyl ether is dimethyl ether.

In another embodiment of this aspect, the reactor comprises a circulating fluidized bed.

In still another embodiment of this aspect, the reaction zone is within a riser.

In yet another embodiment of this aspect of the invention, the effluent contains catalyst fines.

In still yet another embodiment, the analyzing is carried out in less than about five minutes, typically in less than about one minute, say, less than about 30 seconds, e.g., less than about 15 seconds, from a time the single gas phase is provided from said olefins-containing effluent. For present purposes, "from a time the single gas phase is provided" means from a time that a portion of the effluent is taken as a slip stream to the analyzer, and includes travel time to the analyzer; or, in the case of where the IR analyzer directly samples within the reactor effluent stream itself (with no travel time to the analyzer), from the time the analyzer directly measures the effluent stream.

In another embodiment of this aspect, the adjusting is carried out by varying flow rate of said feedstock to the reaction zone, e.g., by adjusting a feed valve.

In still another embodiment, the adjusting is carried out by varying WHSV in the reaction zone, e.g., by changing the position of a slide valve located in a catalyst circulation loop associated with the circulating fluid bed.

In yet another embodiment, the adjusting is carried out by varying the level of coke on catalyst.

In yet another embodiment of this aspect, varying the level of coke on catalyst is carried out by varying WHSV in said reaction zone by changing the position of a slide valve located in a catalyst circulation loop associated with said circulating fluidized bed.

In still yet another embodiment, the slide valve is located at or near the bottom of a riser in which the reaction zone is located.

In another embodiment, the adjusting is carried out by varying reactor temperature.

In yet another embodiment, varying reactor temperature is carried out by varying the amount of said oxygenate-containing feedstock provided as a liquid, relative to the amount of said oxygenate-containing feedstock provided as a vapor, e.g., by adjusting the amount of heat introduced to a feed preheater.

In yet still another embodiment of this aspect of the invention, the analyzing is carried out using FTIR, e.g., by passing a slipstream, taken from said olefins-containing effluent, through an FTIR flow cell.

In one embodiment of this aspect of the invention, the FTIR utilizes near infrared light of a wavelength ranging from about 1000 nm to about 5000 nm.

In another embodiment, the FTIR utilizes middle infrared light of a wavelength ranging from about 5000 nm to about 40000 nm.

In still another embodiment of this aspect of the invention, the substantially consistent effluent composition contains no greater than 20 wt %, typically, no greater than 10 wt %, say, no greater than 5 wt %, oxygenate impurities on a total reactor effluent basis. Typically, such oxygenate impurities are selected from the group consisting of methanol, dimethyl ether, and acetone.

In still yet another embodiment of this aspect of the invention, the single gas phase of the olefins-containing effluent containing methanol and dimethyl ether to be analyzed is obtained by withdrawing a slipstream from the olefins-containing effluent.

In another embodiment, the slipstream is returned as feed to the process after the analyzing.

In yet another embodiment, the slipstream is returned to the olefins-containing effluent after the analyzing.

In another embodiment, the withdrawing and returning is carried out with a sampling loop.

In one embodiment, the withdrawal is continuous.

In still another embodiment, the withdrawal is intermittent.

In yet another embodiment, the slipstream is heated under conditions sufficient to provide a single phase to said analyzing step.

In still yet another embodiment, the analyzing is carried out in less than about five minutes, typically, less than about one minute, say, less than about thirty seconds, e.g., less than about 15 seconds.

In another embodiment, the analyzing is carried out under conditions sufficient to permit the adjusting based on the analyzing to occur within about fifteen seconds from the time the effluent is provided.

In another embodiment, the process of this aspect of the invention further comprises the step of contacting an oxygenate feed with a silicoaluminophosphate (SAPO) molecular sieve catalyst under conditions effective to convert the oxygenate feed to olefins, wherein the conditions comprise a weight hourly space velocity (WHSV) of from about 20 $hr^{-1}$ to about 1000 $hr^{-1}$.

In still another embodiment, the conditions comprise a temperature of at least about 300° C., say, e.g., a temperature in the range of from about 400° C. to about 600° C.

In yet another embodiment, the molecular sieve catalyst is selected from the group consisting of SAPO-17, SAPO-18, SAPO-34, and SAPO-44, e.g., SAPO-34.

In still yet another embodiment, the oxygenate feed is selected from the group consisting of aliphatic alcohols, aliphatic ethers, and aliphatic carbonyl compounds.

In another embodiment, the aliphatic moiety ranges from about 1 to about 10 carbon atoms.

In still another embodiment, the oxygenate feed comprises methanol.

Another aspect of the present invention relates to a process for controlling a circulating fluid bed methanol to olefin reactor to provide a substantially consistent effluent composition, which process comprises: contacting a methanol-containing feedstock in a reaction zone within a riser in the presence of a molecular sieve methanol to olefins conversion catalyst under reactor conditions sufficient to provide an olefins-containing effluent containing methanol and dimethyl ether; analyzing within about one minute a single gas phase of the olefins-containing effluent containing methanol and dimethyl ether to determine methanol concentration and dimethyl ether concentration of said effluent, from a time said single gas phase is directed from said olefins-containing effluent; adjusting the reactor conditions as a function of the determined methanol concentration and said determined dimethyl ether concentration as necessary to provide the consistent effluent composition.

In still another aspect, the present invention relates to an oxygenates to olefin fluidized bed reactor apparatus for converting an oxygenate feed to olefins in a riser reactor having associated therewith a catalyst circulation loop comprising the riser reactor, for circulating catalyst through the riser reactor, the apparatus comprising: an oxygenate feed line communicating with a riser reactor feed inlet to the riser reactor; a slide valve located in the catalyst circulation loop for adjusting space velocity; a riser reactor outlet for riser reactor effluent containing solid catalyst particles and olefins-containing vapor; a disengaging vessel for receiving the riser reactor effluent and separating at least some of the solid catalyst particles from said effluent, the disengaging vessel further comprising a disengaging vessel outlet at an upper portion of the vessel for removing the olefins-containing vapor; a catalyst circulation line running downward from a lower portion of the disengaging vessel to a lower portion of said riser reactor; a regenerator comprising a lower inlet for introducing a regeneration medium, an upper outlet for regenerator flue gas, the regenerator further comprising a catalyst transport line running downwardly from a lower portion of said disengaging vessel to a regenerator catalyst inlet, and a catalyst transport line extending downwardly from a regenerated catalyst outlet and intersecting with a lift gas riser; the lift gas riser having an upper outlet communicating with the disengaging vessel and a lower lift gas inlet; and the reactor apparatus further comprising: a line for withdrawing a slip stream of the riser reactor effluent; an analyzer in communication with the line, for determining alkyl alcohol content and dialkyl ether content of the effluent; and a means for adjusting the slide valve as a function of the alkyl alcohol content and dialkyl ether content of the effluent.

In one embodiment of this aspect of the present invention, the slide valve is located at or near the bottom of the riser reactor.

In another embodiment, the apparatus of this aspect of the present invention further comprises: a line in communication with the analyzer for returning the slipstream to the riser reactor effluent.

In still another embodiment, the analyzer is calibrated by comparing to results obtained using a gas chromatograph. The gas chromatograph can employ any suitable detector means known to those skilled in the art, e.g., one selected from the group consisting of flame ionization detector, mass spectroscopy detector, thermal conductivity detector, pulsed discharge electron capture detector, photometric detector, argon detector, triode detector, helium detector, pulsed helium discharge detector, and electron capture detector.

In another embodiment, the analyzer is calibrated by preparing a liquid blend standard, flashing the liquid blend standard, and analyzing the resulting vapor as a calibration standard.

In yet another embodiment, the analyzer comprises an FTIR flow cell.

In still yet another embodiment, the FTIR flow cell utilizes near infrared light of a wavelength ranging from about 1000 nm to about 5000 nm.

In another embodiment, the FTIR flow cell utilizes middle infrared light of a wavelength ranging from about 5000 nm to about 40000 nm.

In yet another embodiment, the line for withdrawing a slipstream comprises a heater capable of providing said slipstream to said analyzer in a single gas phase.

In still another embodiment, the apparatus further comprises: a preheater for the oxygenate-containing feed; and a means for adjusting heat input to the preheater as a function of the alkyl alcohol content and dialkyl ether content of the effluent.

In yet still another embodiment, the apparatus further comprises: a flow controller for regulating the flow of the oxygenate feed to the riser reactor; and a means for adjusting WHSV in the riser reactor by adjusting the flow controller as a function of the alkyl alcohol content and dialkyl ether content of the effluent.

DETAILED DESCRIPTION

Oxygenate to Olefins Reactor Apparatus

Figure 1:
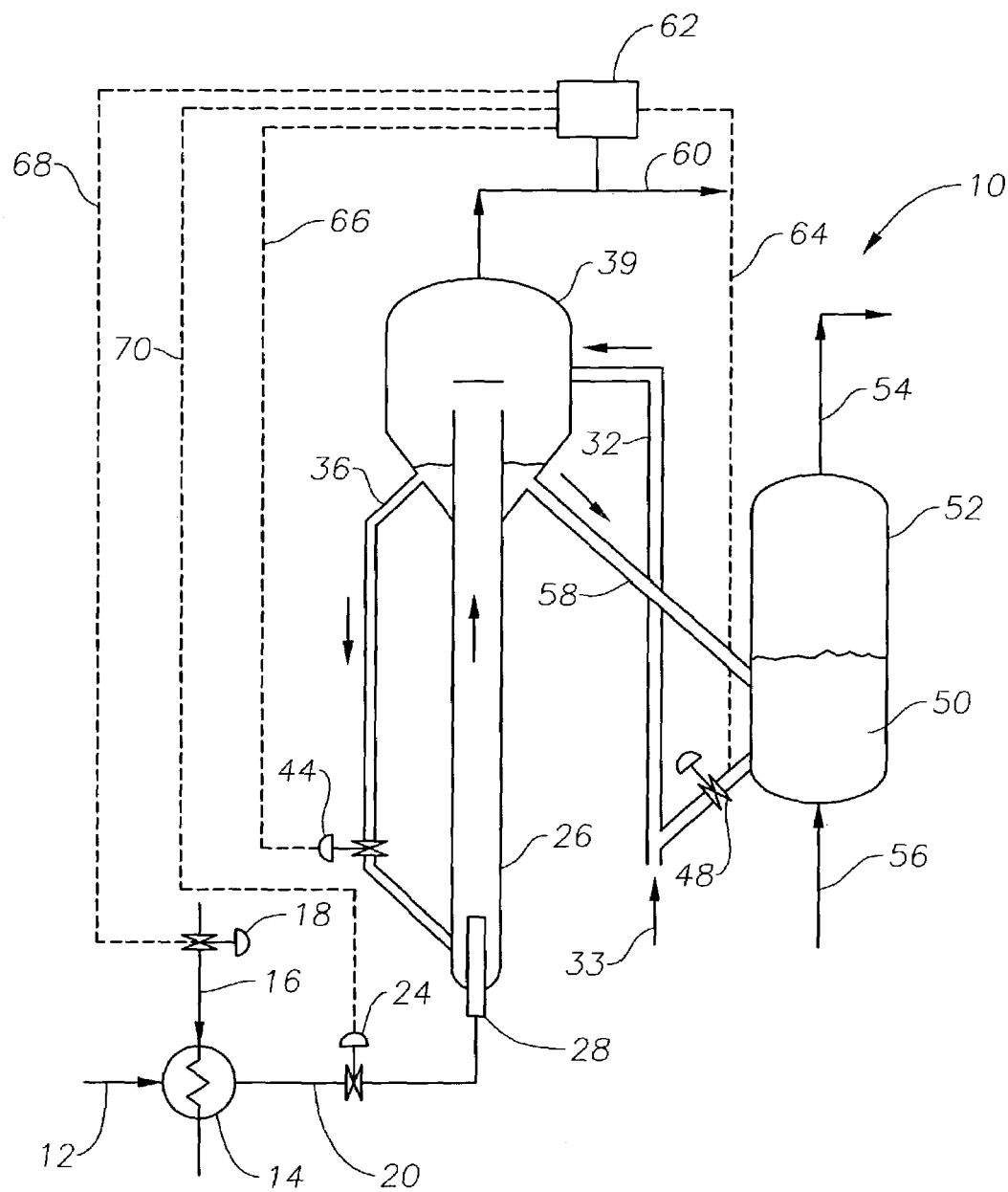
FIG. 1 depicts an oxygenates to olefins circulating fluid bed reactor control scheme in accordance with the present invention.

The process for converting a feedstock, especially a feedstock containing one or more oxygenates, in the presence of a molecular sieve catalyst composition according to the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Liquid feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s). Preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

Oxygenate to Olefins Process

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, incorporated herein by reference, addition of aromatics) or mixtures thereof, preferably propylene, butylene, pentylene, and other hydrocarbons having 4 or more carbon atoms, or mixtures thereof.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is selected from group 13 (IIIA), groups 8, 9 and 10 (VIII) elements) from the Periodic Table of Elements), and a molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kpaa) to about 250 psia (1724 kPaa), more preferably from about 25 psia (172 kPaa) to about 150 psia (1034 kPaa), and most preferably from about 30 psia (207 kpaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are disclosed in U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system, where an excess of oxygen is maintained in the regenerator. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator where an excess flow of catalyst is maintained such that the coke is only partially removed per pass through the regenerator. This is referred to as the partial regeneration mode.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 weight percent coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels of individual catalyst particles.

The present invention solves the current needs in the art by providing a method for converting a feed including an oxygenate to a product including a light olefin. The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

A preferred embodiment of a reactor system for the present invention is a circulating fluid bed reactor with continuous regeneration, similar to a modern fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently or continuously, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a desired coke content on catalyst in the reactor.

Reactor Control

As noted earlier, the operation of an oxygenates to olefins reactor can be optimized by controlling several important variables associated with the reactor.

Control of the reactor can be effected by measuring a variable, comparing the variable with its corresponding optimal value, selected depending on the outcome desired, deriving a signal based on the comparison, and utilizing the signal to manipulate a manipulated variable. An analogy to this control scheme can be found in speed control devices commonly found in automobiles, wherein the speed represents the measured variable, the speed setting represents the corresponding optimal value and the throttle position represents the manipulated variable. Measured speed is compared with the speed setting to provide a signal that is then used to manipulate the throttle setting to provide a measured value (speed) approximating the optimal value.

Optimal value for present purposes can be set by factoring in desired outcomes of the reactor operator, especially in terms of product characteristics, such as lower olefins content, e.g., ethylene selectivity or propylene selectivity, and/ or oxygenate conversion. Other desired outcomes by the operator, or reactor operating limitations, e.g., temperature, pressure, and space velocity may be used to set optimal values or ranges of values for a measured variable. Additional guidance in setting such values can be found in U.S. Pat. No. 4,076,796, U.S. Pat. No. 6,287,522 (dual riser), *Fluidization Engineering*, D. Kunii and O. Levenspiel, Robert E. Krieger Publishing Company, New York, N.Y. 1977, *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), U.S. patent application Ser. No. 09/564,613 filed May 4, 2000 (multiple riser reactor), which are all herein fully incorporated by reference.

The present invention provides a simple and effective method for controlling oxygenates to olefins reactor systems so that a consistent reactor effluent stream can be obtained. Stream fluctuations can overload separations used to obtain polymer grade olefin streams. While conversion can be determined from many types of effluent stream analyses, it is difficult to obtain such an analysis fast enough for the results to be useful for oxygenates to olefins reactor control. Accordingly, the present invention provides a process to control an oxygenates to olefin reactor using a real time effluent stream analysis, or near real time effluent stream analysis wherein the sampled stream is analyzed within at least about one minute, say, within at least about 30 seconds, e.g., within about 15 seconds. By using an on-line IR system, the present invention quantifies oxygenate content, e.g., alcohol and/or ether content, say, alkyl alcohol and/or dialkylether content, e.g., methanol and dimethyl ether concentration in the effluent in order to determine conversion in the reactor. Once conversion is determined, adjustment to the oxygenates to olefin conversion process can be made in order to provide a desired substantially consistent reactor effluent. Such adjustment can be carried out by adjusting weight hourly space velocity in the reactor riser, e.g., by adjusting the riser slide valve. This will minimize perturbations in the reactor conversion from the desired set point.

When producing olefins using a Methanol to Olefins (MTO) reactor, one also obtains methanol and dimethyl ether along with many other oxygenated and hydrocarbon compounds. Typically a series of separation processes (usually distillations) are performed to obtain specific olefin streams (i.e., ethylene, propylene, etc.). Frequently, the desired use for these olefins is synthesis of polymers. For such applications, it is necessary to have very low levels of oxygenate and non-oxygenate impurities as these poison the polymerization catalysts. These separations, downstream of the reactor, are sized so that they can handle removing certain levels of impurities. It is therefore undesirable to have variations in the reactor effluent that can disrupt the downstream separation processes. In order to prevent this, one would like to control the MTO reactor to minimize the reactor effluent composition perturbations.

Oxygenate to olefins conversion can be defined in various ways. For an embodiment of the present invention, methanol conversion to olefins can be based on the following equation:

$$\text{Conversion} = 1 - \frac{(W_{MeOH,effluent})(14/32) + (W_{DME,effluent})(28/46)}{100(14/32)}$$

where $W_{MeOH,effluent}$ and $W_{DME,effluent}$ are the weight percent of methanol and dimethyl ether, respectively, in the total reactor effluent on a wet basis. The ratios of 14/32 and 28/46 are the hydrocarbon weight fraction of methanol and dimethyl ether. The definition of conversion above is on a hydrocarbon basis.

In order to calculate conversion from this equation, one needs a measurement of the concentrations of methanol and dimethyl ether in the reactor effluent. While there are many ways that one can obtain these measurements, both on- and off-line, it is difficult to measure these component concentrations in real time (which for present purposes includes near real time, i.e., within at least about one minute). The value in being able to determine conversion in real time is that information is available to allow for more frequent reactor adjustments. Specifically, the reactor effluent can be maintained more consistent by adjusting the slide valve at the bottom of the riser, which in term changes the WHSV in the riser.

In choosing an analytical method there are many complicating factors to consider. First, the reactor effluent is hot, typically about 482° C. (900° F.), at 276 kPaa (40 psia) and exists as a gas phase only. The reactor effluent can be cooled to about 150° C. (302° F.), at 276 kPaa (40 psia) before condensation occurs.

It is preferred to quantify the methanol and dimethyl ether in a single gas phase as opposed to two phases. Analyzing a single gas phase will require only one analysis and one avoids the arduous task of having to quantify the ratio of gas to liquid phase.

There are several methods available to determine the reactor effluent stream composition. The most accurate and robust type of analysis is to use gas chromatography (GC) with a flame ionization detector (FID). Other detectors can be used besides a FID. The drawback with most chromatography techniques is that they require long periods of time to quantify the methanol and dimethyl ether concentrations (close to an hour). Using analytical measurements this infrequent to control the reactor conversion results in large deviations from the desired conversion. A second complication in performing this analysis is that the reactor effluent stream contains catalyst fines. These need to be removed prior to stream analysis to prevent plugging of tubing to the GC as well as damaging the GC column.

The present invention utilizes Fourier Transform mid Infra Red (FT-IR) spectroscopy as the detection technique. In one embodiment of the present invention, a slipstream of the reactor effluent is passed through a FT-IR flow cell where the methanol and dimethyl ether concentrations are determined. This analysis is done on a slipstream that is heated (as is the flow cell) to prevent condensation. This way, the slipstream is a single gas phase having the same composition as the reactor effluent. This analysis can be done over a period of seconds. Indeed, the greatest delay in the measurement arises from delay in the sample loop used to draw sample from the reactor and into the FTIR flow cell. Using the technique of the present invention, one can make adjustments to the reactor with less than a minute delay from the time the effluent stream leaves the reactor.

For present purposes, the term "conversion" is defined on the basis of disappearance of reactant. In the specific case of methanol to olefins (MTO), the reactant is generally defined as the total of methanol plus dimethyl ether (DME). Thus, for the purposes of calculating conversion, both the methanol and DME are measured in the reactor effluent and combined to determine the disappearance of reactant.

For present purposes, "space velocity" is defined here on a weight hourly basis, and has units of $hr^{-1}$.

A preferred embodiment of a riser reactor configuration for use in the present invention is depicted generally as 10 in FIG. 1. A methanol feed passed via line 12 is at least partially vaporized in a preheater 14 wherein heat is provided through a heating medium via line 16, controlled by control valve 18. The preheated feed is passed via line 20 and its flow controlled by feed flow control valve 24 for the purpose of controlling methanol feed flow to the riser reactor 26 via feed inlet 28. Control valve 18 is manipulated for the purpose of controlling heat input to the feed by the heating medium in order to control feed preheat rate.

The methanol feed is mixed in the bottom of riser reactor 26 with regenerated catalyst introduced via line 32 along with lift gas via line 33, to the disengaging vessel 34 and thence via line 36 along with coked catalyst collected by the disengaging vessel 34. The disengaging vessel separates solid catalyst particles that are circulated via line 36 to the bottom of riser reactor 26. Valve 44 controls the catalyst flow to the bottom of the riser reactor 26 and thus the WHSV in the reaction zone.

Catalyst circulation is controlled by slide control valve 48 to regulate the flow of regenerated catalyst 50 from regenerator 52 and thus the level of coke on the catalyst in the riser. Regenerator flue gas is taken off via line 54, regenerator air is supplied to the reactor via line 56 and coked catalyst is directed from disengaging vessel 34 to regenerator 52 via line 58. Reactor effluent exits disengaging vessel 34 via line 60.

A slip stream of oxygenates to olefins reactor effluent is taken from line 60 to an IR analyzer 62 which determines the concentration of methanol and dimethyl ether in the effluent and which further provides a signal via: line 64 which controls slide valve 48 to adjust coke level on catalyst in the reactor riser 26 (and thus catalyst activity); and/or line 66 which controls slide valve 44, which adjusts WHSV conditions in the reactor riser 26; and/or line 68 which controls valve 18 to regulate the input of heat to preheater 14 to control temperature conditions within the reactor riser 26, and/or line 70 which controls valve 24 which adjusts oxygenate feedstock flow rate to the reactor riser 26 (and thus WHSV).

EXAMPLE

Figure 2:
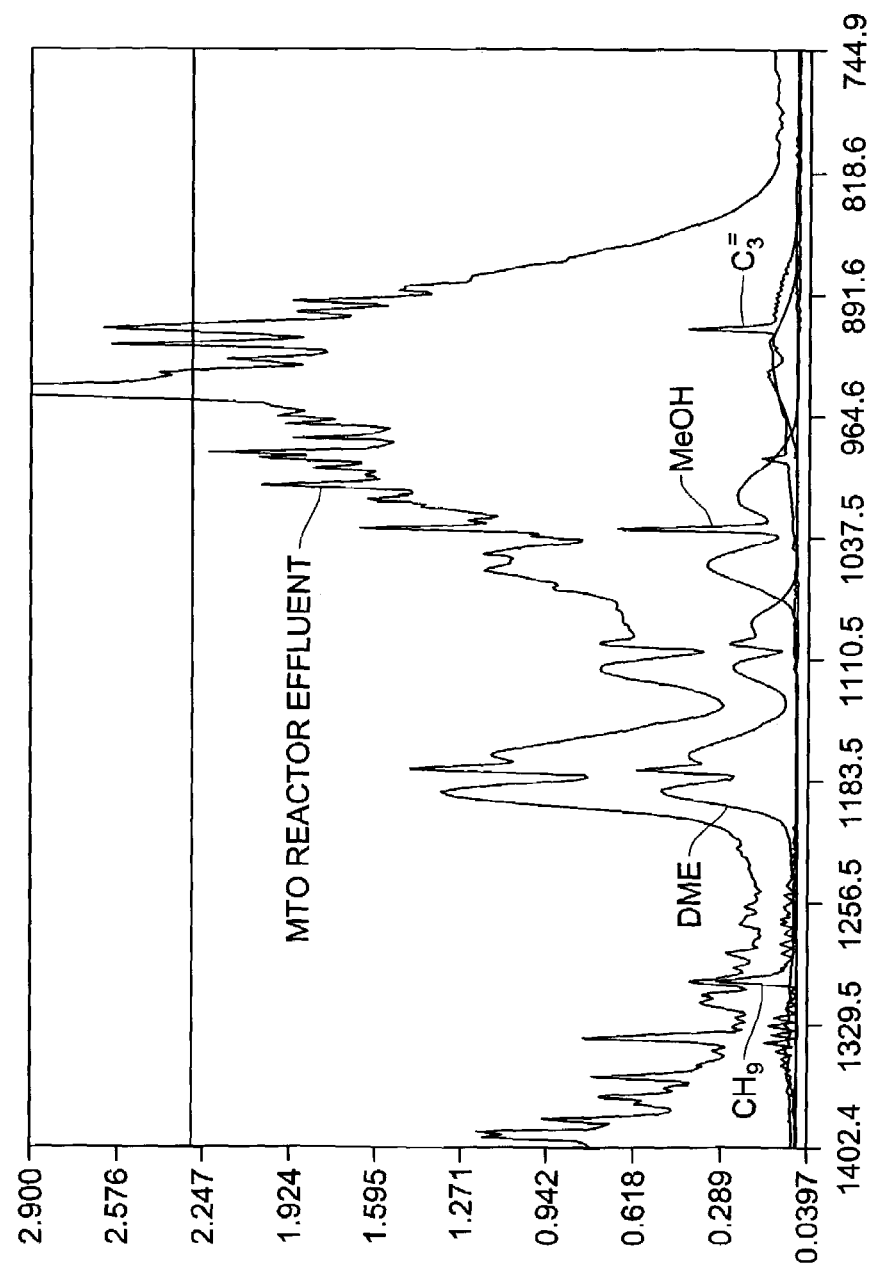
FIG. 2 depicts IR spectra of MTO reactor effluent and for dimethyl ether, methanol, propylene, and methane (as labeled).

A product demonstration was performed with a mid IR system. A heated slipstream of reactor effluent was fed to an IR flow cell through ⅛ inch heat traced silanized stainless steel tubing. The gas stream was maintained at approximately 150° C. and approximately 450 kPaa (65 psia). The mid IR system consisted of a cell with a 3 cm path and 4 mm barium fluoride windows. The resulting spectrum is shown in FIG. 2 in which intensity (in absorbance) is plotted on the y-axis against the frequency (in wavenumbers) on the x-axis. The gray spectrum corresponds to that of an MTO reactor effluent using the aforementioned IR system. Along with this spectrum are shown standard spectra for the following pure components: DME, methanol, propylene and methane. The peak height corresponds to the concentration of each species present in the stream. Taller peaks correspond to higher concentrations of each component. This system was able to measure the concentration of dimethyl ether and methanol in sections of their spectra that had little or no interference from other compounds. Ethylene and propylene could be seen in the spectra and their concentration could be approximated, but with limited accuracy due to overlap with other peaks.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. A process for controlling an oxygenates to olefin reactor to provide a substantially consistent effluent composition, which process comprises:
   contacting an oxygenate-containing feedstock in a reaction zone in the presence of a molecular sieve oxygenate to olefins conversion catalyst under reactor conditions sufficient to provide an olefins-containing effluent containing alkyl alcohol and dialkyl ether;
   analyzing a single gas phase of said olefins-containing effluent containing alkyl alcohol and dialkyl ether to determine alkyl alcohol concentration and dialkyl ether concentration of said effluent;
   adjusting said reactor conditions as a function of said alkyl alcohol concentration and said dialkyl ether concentration, as necessary to provide said substantially consistent effluent composition,
   wherein said adjusting of reactor conditions is carried out by one or more of:
   a) varying WHSV within said reaction zone;
   b) varying the level of coke which deposits on said conversion catalyst within said reaction zone;
   c) varying the reaction temperature within said reaction zone;
   d) varying the amount of said oxygenate-containing feedstock provided to said reaction zone as a liquid, relative to the amount of said oxygenate-containing feedstock provided to said reaction zone as a vapor; or
   e) varying heat input to a feed pre-heater used for pre-heating said oxygenate-containing feedstock prior to said contacting with said conversion catalyst; and
   wherein said analyzing is carried out under conditions sufficient to permit said adjusting based on said analyzing to occur within about fifteen seconds from the time said effluent is provided.

2. The process of claim 1 wherein said oxygenate-containing feedstock comprises methanol, said alkyl alcohol is methanol and said dialkyl ether is dimethyl ether.

3. The process of claim 2 wherein said reactor comprises a circulating fluidized bed.

4. The process of claim 3 wherein said reaction zone is within a riser.

5. The process of claim 4 wherein said effluent contains catalyst fines.

6. The process of claim 3 wherein said analyzing is carried out in less than about five minutes from a time said single gas phase is provided from said olefins-containing effluent.

7. The process of claim 3 wherein said analyzing is carried out in less than about one minute from a time said single gas phase is provided from said olefins-containing effluent.

8. The process of claim 3 wherein said analyzing is carried out in less than about 30 seconds from a time said single gas phase is provided from said olefins-containing effluent.

9. The process of claim 3 wherein said analyzing is carried out in less than about 15 seconds from a time said single gas phase is provided from said olefins-containing effluent.

10. The process of claim 3 wherein said adjusting is carried out by varying WHSV in said reaction zone.

11. The process of claim 3 wherein said adjusting is carried out by varying WHSV in said reaction zone by changing the position of a slide valve located in a catalyst circulation loop associated with said circulating fluidized bed.

12. The process of claim 11 wherein said slide valve is located at or near the bottom of a riser in which said reaction zone is located.

13. The process of claim 3 wherein said adjusting is carried out by varying WHSV in said reaction zone by changing the flow rate of said oxygenate feedstock to said reaction zone.

14. The process of claim 3 wherein said adjusting is carried out by varying the level of coke on said catalyst.

15. The process of claim 14 wherein said varying the level of coke on catalyst is carried out by varying WHSV in said reaction zone by changing the position of a slide valve located in a catalyst circulation loop associated with said circulating fluidized bed.

16. The process of claim 3 wherein said adjusting is carried out by varying reactor temperature.

17. The process of claim 16 wherein said varying reactor temperature is carried out by varying the amount of said oxygenate-containing feedstock provided as a liquid, relative to the amount of said oxygenate-containing feedstock provided as a vapor.

18. The process of claim 16 wherein said varying reactor temperature is carried out by adjusting the amount of heat introduced to a feed preheater.

19. The process of claim 3 wherein said adjusting is carried out by varying heat input to a feed preheater for preheating said oxygenate-containing feedstock prior to said contacting.

20. The process of claim 3 wherein said analyzing is carried out using FTIR.

21. The process of claim 20 wherein said analyzing is carried out by passing a slip stream, taken from said olefins-containing effluent, through an FTIR flow cell.

22. The process of claim 20 wherein said FTIR utilizes near infrared light of a wavelength ranging from about 1000 nm to about 5000 nm.

23. The process of claim 22 wherein said FTIR utilizes middle infrared light of a wavelength ranging from about 5000 nm to about 40000 nm.

24. The process of claim 3 wherein said substantially consistent effluent composition contains no greater than 20 wt % oxygenate impurities on a total reactor effluent basis selected from methanol, dimethyl ether, and acetone.

25. The process of claim 3 wherein said substantially consistent effluent composition contains no greater than 10 wt % oxygenate impurities on a total reactor effluent basis selected from methanol, dimethyl ether, and acetone.

26. The process of claim 3 wherein said substantially consistent effluent composition contains no greater than 5 wt % oxygenate impurities on a total reactor effluent basis selected from methanol, dimethyl ether, and acetone.

27. The process of claim 3 wherein said single gas phase of said olefins-containing effluent containing methanol and dimethyl ether to be analyzed is obtained by withdrawing a slip stream from said olefins-containing effluent 28. The process of claim 27 wherein said slip stream is returned as feed to said process after said analyzing.

29. The process of claim 27 wherein said slip stream is returned to said olefins-containing effluent after said analyzing.

30. The process of claim 28 wherein said withdrawing and returning is carried out with a sampling loop.

31. The process of claim 27 wherein said withdrawal is continuous.

32. The process of claim 27 wherein said withdrawal is intermittent.

33. The process of claim 27 wherein said slip stream is heated under conditions sufficient to provide a single phase to said analyzing step.

34. The process of claim 1 further comprising the step of contacting an oxygenate feed with a silicoaluminophosphate (SAPO) molecular sieve catalyst under conditions effective to convert said oxygenate feed to olefins, wherein said conditions comprise a weight hourly space velocity (WHSV) of from about 20 hr$^{-1}$ to about 1000 hr$^{-1}$.

35. The process of claim 1 wherein said conditions comprise a temperature of at least about 300° C.

36. The process of claim 1 wherein said conditions comprise a temperature in the range of from about 400° C. to about 600° C.

37. The process of claim 1 wherein said molecular sieve catalyst is selected from the group consisting of SAPO-17, SAPO-18, SAPO-34, and SAPO-44.

38. The process of claim 1 wherein said molecular sieve catalyst is SAPO-34.

39. The process of claim 1 wherein said oxygenate feed is selected from the group consisting of aliphatic alcohols, aliphatic ethers, and aliphatic carbonyl compounds.

40. The process of claim 39 wherein said aliphatic moiety ranges from about 1 to about 10 carbon atoms.

41. The process of claim 40 wherein said oxygenate feed comprises methanol.

42. A process for controlling a circulating fluid bed methanol to olefin reactor to provide a substantially consistent effluent composition, which process comprises:

contacting a methanol-containing feedstock in a reaction zone within a riser in the presence of a molecular sieve methanol to olefins conversion catalyst under conditions sufficient to provide an olefins-containing effluent containing methanol and dimethyl ether;

analyzing within about five minutes a single gas phase of said olefins-containing effluent containing methanol and dimethyl ether to determine methanol concentration and dimethyl ether concentration of said effluent, from a time said single gas phase is provided from said olefins-containing effluent;

adjusting reactor conditions as a function of said determined methanol concentration and said determined dimethyl ether concentration as necessary to provide said substantially consistent effluent composition, wherein said adjusting of reactor conditions is carried out by one or more of:

a) varying WHSV within said reaction zone;

b) varying the level of coke which deposits on said conversion catalyst within said reaction zone;

c) varying the reaction temperature within said reaction zone;

d) varying the amount of said methanol-containing feedstock provided to said reaction zone as a liquid, relative to the amount of said methanol-containing feedstock provided to said reaction zone as a vapor; or e) varying heat input to a feed pre-heater used for pre-heating said methanol-containing feedstock prior to said contacting with said conversion catalyst; and wherein said analyzing is carried out under conditions sufficient to permit said adjusting based on said analyzing to occur within about fifteen seconds from the time said effluent is provided.

43. The process of claim 42 wherein said analyzing is within about one minute.

* * * * *